USA006928907B2

(12) United States Patent  (10) Patent No.: US 6,928,907 B2
Casabonne et al.  (45) Date of Patent: Aug. 16, 2005

(54) DYNAMOMETRIC KEY

(75) Inventors: Thierry Casabonne, Bordeaux (FR); Dominique Mariaulle, Le Haillan (FR)

(73) Assignee: Satelec SA, Merignac (FR)

( * ) Notice: Subject to any disclaimer, the term of this patent is extended or adjusted under 35 U.S.C. 154(b) by 0 days.

(21) Appl. No.: 10/415,670

(22) PCT Filed: Nov. 28, 2001

(86) PCT No.: PCT/FR01/03766

§ 371 (c)(1),
(2), (4) Date: Oct. 20, 2003

(87) PCT Pub. No.: WO02/43927

PCT Pub. Date: Jun. 6, 2002

(65) Prior Publication Data

US 2004/0055425 A1 Mar. 25, 2004

(30) Foreign Application Priority Data

Nov. 28, 2000 (FR) .............................. 00 15316

(51) Int. Cl.[7] ............................................ B25B 23/159
(52) U.S. Cl. ............................ 81/483; 81/475; 81/476
(58) Field of Search .................... 81/483, 475, 478, 81/467, 480, 435, 37, 41

(56) References Cited

U.S. PATENT DOCUMENTS

| 4,219,035 | A | * | 8/1980 | Deconinck | .................... | 211/65 |
| 6,021,694 | A | * | 2/2000 | Beger | ......................... | 81/483 |
| 6,186,785 | B1 | * | 2/2001 | Rogers et al. | ............. | 433/141 |
| 6,296,656 | B1 | * | 10/2001 | Bolduc et al. | ............. | 606/213 |

FOREIGN PATENT DOCUMENTS

| DE | 21 63 109 | 6/1973 |
| FR | 2 184 237 | 12/1973 |
| WO | WO 00 38589 | 7/2000 |

* cited by examiner

Primary Examiner—Joseph J. Hail, III
Assistant Examiner—Alvin J Grant
(74) Attorney, Agent, or Firm—Young & Thompson

(57) ABSTRACT

The invention concerns a dynamometric key designed in particular for fixing an insert (22) on a handpiece (23). Said dynamometric key is characterized in that it consists of a grip element (3), and a securing element (5), said two elements being linked in frictional rotation via a spring (1) whereof the end coils have been assembled, so as to provide it with a globally toroidal shape.

11 Claims, 2 Drawing Sheets

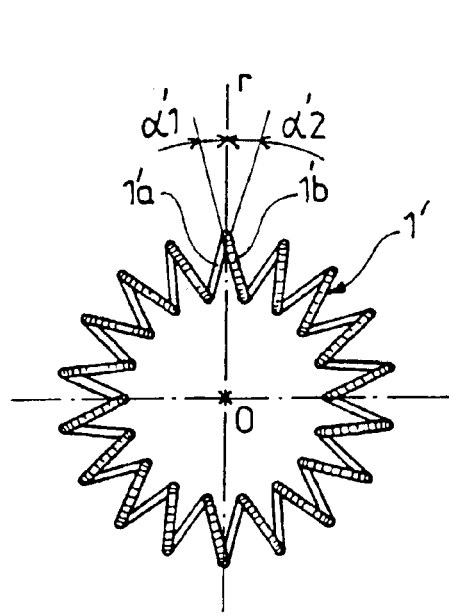 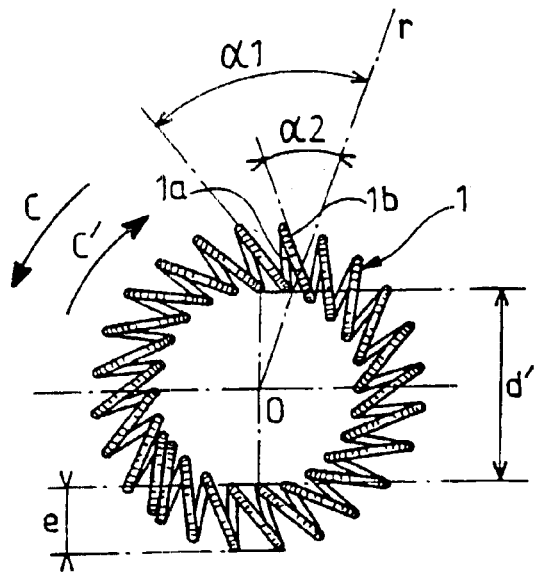
FIG.1a  FIG.1b
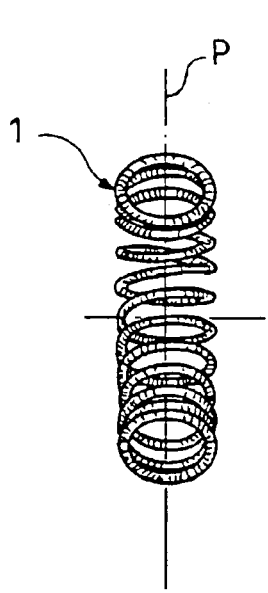 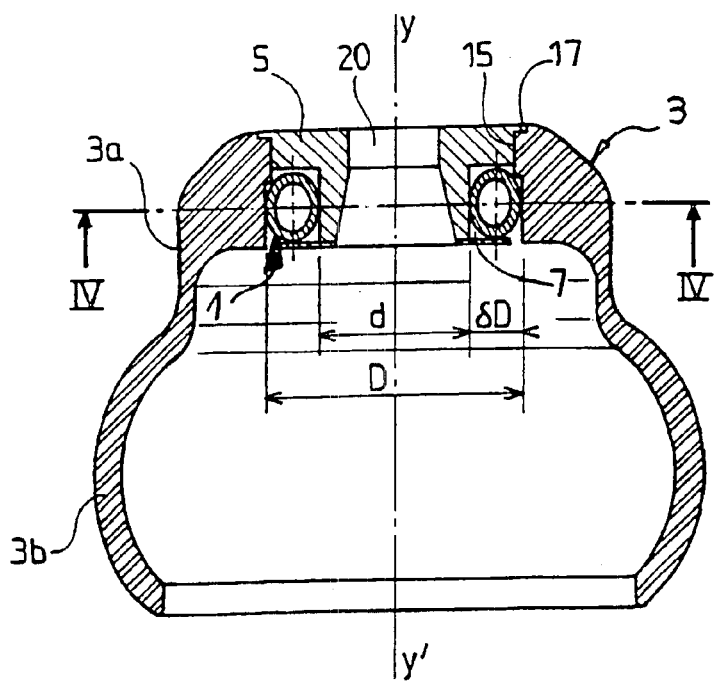
FIG.1c  FIG.2

DYNAMOMETRIC KEY

BACKGROUND OF THE INVENTION

The present invention relates to a dynamometric key and more particularly to a key of this type intended to ensure tightening and loosening of an insert on a dental handpiece.

Dynamometric keys used in industry, which are adapted to deliver considerable tightening and even loosening moments, are known. Such dynamometric keys are constituted by complex mechanical elements which are easy to employ in devices of respectable volume but which are particularly difficult and expensive to manufacture as soon as it is desired to transpose them to a smaller scale.

U.S. Pat. No. 6,021,694 in particular discloses a dynamometric key intended for surgical use which is essentially constituted by a tubular element containing a linear helicoidal spring of which the level of compression is determined by means of an adjusting screw. This compression spring acts by friction on the outer part of the ball bearing housing, which retransmits to the end of the key a moment determined by its level of friction. Such a device is difficult to use in certain domains of applications and in particular in that of the dental domain by reason of the considerable lever arm constituted by this device which gives it a large volume which is incompatible with the techniques used.

SUMMARY OF THE INVENTION

The present invention has for its object to propose a dynamometric key which is particularly compact and simple in construction and which, moreover, makes it possible, during use, to protect the hand of the practitioner who is actuating said key, from the end of the tool.

The present invention thus has for it object a dynamometric key intended for tightening/loosening an element to be fixed, particularly an insert on a dental handpiece, characterized in that it is constituted by a grip element and a securing element which is linked at least in rotation with the element to be fixed, the grip element and the securing element being linked in frictional rotation via a spring of helicoidal type of which the end turns have been assembled so as to provide it with a substantially toroidal shape, the two parts of the same turn, located on either side of a median plane, are inclined on the same side with respect to the radial axis of the spring.

The turns of the spring, when the latter is in the free state, will preferably have a flattened shape along its radial axis, this flattened shape being able to take the form of an ellipsis in particular.

The securing element may preferably be constituted by a cylindrical element comprising a cylindrical outer groove in which the spring is fitted, the base diameter of the groove being slightly greater than the inner diameter of the spring when it is in the free state.

The grip element may have a cylindrical recess hollowed out therein, of which the diameter defines, with the diameter of the securing element, a spacing less than the height of the turns when the spring is in the free state, so as to compress them.

In a form of embodiment of the invention, the grip element will comprise two parts, namely a substantially cylindrical upper part and a lower part substantially in the form of a bell.

The internal volume of the bell-shaped part may preferably envelop the tool, whatever the positioning thereof inside the dynamometric key.

In this form of embodiment, the immobilization, in the axial sense, of the securing element with respect to the grip element, will be ensured in particularly simple manner by the spring itself, which, apart from the very simplicity of this mechanism, allows rapid assembly and dismantling of the device.

According to the invention, it has been observed that the moment which it is necessary to exert in order to rotate the securing element by driving it in rotation by means of the grip element, was greater in one direction of rotation than in the other. Under these conditions, it will be understood that, if the direction of rotation generating the lower moment corresponds to the moment for tightening the insert on the handpiece, the other direction of rotation will apply a greater moment which, if it is well adjusted, will ensure loosening of the insert from the handpiece.

It has been observed that, for a spring of given dimensions and mechanical characteristics, the tightening/loosening moment was increased by giving the housings, between which the spring is disposed, a dimension ensuring a compression of the turns thereof in a substantially radial direction.

BRIEF DESCRIPTION OF THE DRAWINGS

A form of embodiment of the present invention will be described hereinafter by way of non-limiting example, with reference to the accompanying drawings, in which:

FIG. 1a is a plane view of a helicoidal spring according to the prior state of the art, of which the two ends have been secured so as to provide it with a globally toric shape.

FIG. 1b is a plan view of a spring used in the dynamometric key according to the invention.

FIG. 1c is a side view of the spring shown in FIG. 1b.

FIG. 2 is a view in axial and longitudinal section of the dynamometric key according to the invention.

DETAILED DESCRIPTION OF THE PREFERRED EMBODIMENTS

FIG. 1a shows a helicoidal spring 1' of conventional type of which the ends have been assembled so as to provide it with a globally toric shape. It is seen that the two half-turns 1'a and 1'b which are located on either side of a median plane P (FIG. 1c) lie substantially symmetrically with respect to a radial axis Or when the spring is observed in plan (FIG. 1a), and the respective half-turns 1'a and 1'b form equal angles α'1 and α'2 with respect to axis Or.

As for the device according to the invention, it resorts to a spring of the same type likewise of globally toric form but in which the two half-turns 1a and 1b are inclined on the same side of the radial axis Or. According to the invention, as shown in FIGS. 1b and 1c, the respective half-turns 1a and 1b form different angles α1 and α2 with the radial axis Or.

It has been ascertained that the springs of this type, when they were used as intermediate elements to transmit a torsional moment, had the property of transmitting, before slide, a moment C of a certain given fixed value when their rotation was effected in one direction and a moment of another, lower, given fixed value C', when the rotation was effected in the other direction, the two absolute values C and C' of these two moments being, of course, a function of the materials with which they are placed in contact. It has been ascertained that the higher moment C was transmitted when a relative movement of the spring 1 was made with respect to the component with which it is in contact, in the direction of arrow C, i.e. when the relative displacement of the spring was effected in the direction followed when passing from an inner part of a turn and going towards its outer part, i.e. in the direction of arrow C in FIG. 1b.

Springs of the same nature are known from the prior state of the art and are used for numerous applications, but they have not been used up to the present time for transmitting determined respective fixed moments of rotation.

Figure 3:
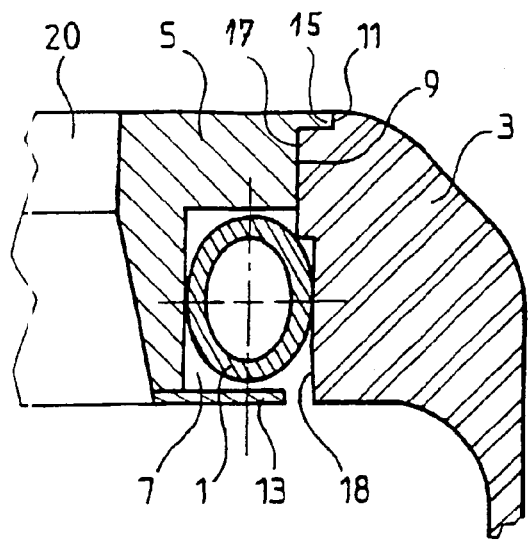
FIG. 3 is an enlarged partial view of the upper part of the dynamometric key shown in FIG. 2.
Figure 4:
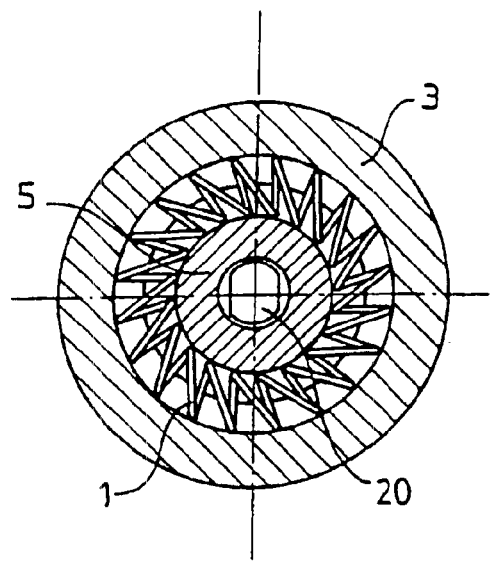
FIG. 4 is a view in cross section of the dynamometric key shown in FIG. 2 along line IV—IV thereof.

The dynamometric key according to the invention, which is shown in FIGS. 2 to 4, is essentially constituted by an outer ring 3 made of aluminium, which constitutes a grip element, and by an inner core 5 made of stainless steel, between which is arranged a spring 1 of the type described previously, and which is shown in FIGS. 1b and 1c.

The ring 3 and the core 5 might, of course, be made of any other material and in particular of plastics material or ceramics.

Figure 6:
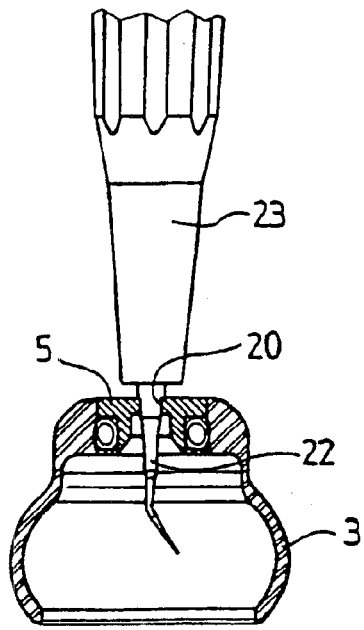
FIG. 6 is a view in partial longitudinal section of a handpiece, on the insert of which the dynamometric key according to the invention is positioned.

The inner core 5 is constituted by a cylindrical element which has a circular groove 7 hollowed out therein whose inner diameter d is such as to receive the spring 1 while exerting a slight stress thereon. To that end, the diameter d will be slightly greater than the inner diameter d of the spring 1 when the latter is in the free state. Above the groove 7, the core 5 comprises a first boss 9 followed by a second boss 11 of larger diameter and of lesser thickness. Below the groove 7 it terminates in a circular plate 13. In its upper part, the core 5 comprises a slot 20 which is intended to ensure the mechanical link in rotation of the dynamometric key according to the invention with the device for tightening/loosening an insert 22 of a handpiece 23 for example, as shown in FIG. 6.

The outer ring 3 comprises a first part 3a (upper in the drawing) of substantially cylindrical shape, followed by a second part 3b (lower in the drawing) in the form of a bell. The cylindrical part 3a receives the core 5 which will be previously provided with the spring 1. To that end, it comprises cylindrical upper recesses 15 and 17 respectively intended to receive the bosses 9 and 11. Under the recess 17, a cylindrical housing 18 has been made, whose diameter D cooperates with the diameter d of the core 5 in order to define therebetween a spaced apart relationship $\delta D=(D-d)/2$ whose value determines the state of compression of the turns of the spring 1.

Figure 5:
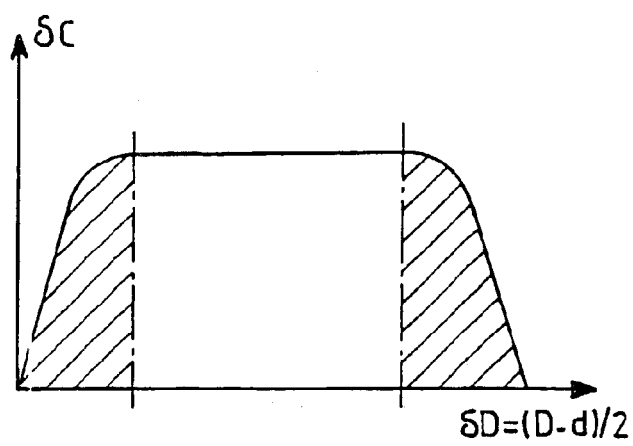
FIG. 5 is a curve representing the variation of the difference in moment transmitted by a spring in its two respective directions of rotation as a function of the deformation exerted on its turns in the radial sense.

In effect, it has been ascertained that, when the turns of springs of the spring 1 type were subjected to a radial compression, not only the absolute value C and C' of the moments of rotation transmitted was increased, but the difference $\delta C=C-C'$ of these moments for opposite directions of rotation was also varied. By measurements, it was established that the value of this difference $\delta C$ was connected with the value of the compression of the turns of the spring $\delta D=(D-d)/2$, and this for a spring 1 of determined mechanical characteristics, depending on a function of which the course is shown in the curve of FIG. 5.

It has also been ascertained that, for a given radial compression level, the transmitted moments C and C' were higher when the diameter of the wire constituting the turns was greater.

By adjusting the spaced apart relationship $\delta D=(D-d)/2$, and this by adjusting the dimensions of the diameters D and d, it is thus possible to control the difference $\delta C$ which exists between the values of the moments which may be applied with the dynamometric key according to the invention.

The latter is particularly interesting to ensure a tightening, with a determined given moment C', of an "insert" 22, i.e. of a tool on a dental handpiece 23.

As shown in FIG. 6, it suffices to that end for the practitioner to introduce the insert 22 in the slot 20 so as to ensure its link in rotation with the core 5, then to animate the ring 3 by a movement of rotation. To that end, steps will be taken for the spring 1 to be positioned on the core 5 so that, by rotating in the direction of tightening, the moment C' of lower value is applied to the insert, and that, by rotating in the direction of loosening, the moment C of higher value is then applied, so as to ensure unscrewing.

It will be noted that the dynamometric key according to the invention presents the advantage, by a simple turn of the spring 1, of allowing its direction of tightening to be reversed, which makes it possible to adapt it easily and rapidly to an insert/handpiece device of which the direction of the pitch is reversed with respect to the usual direction.

Furthermore, the shape of the dynamometric key according to the invention allows the practitioner to operate in complete safety, insofar as his hand controlling the rotation of the grip element is protected from the insert by the bell-shaped part 3b.

What is claimed is:

1. Dynamometric key intended for tightening/loosening an element to be fixed, particularly an insert on a dental handpiece, said dynamometric key comprising:
    a grip element and a securing element which is linked at least in rotation with the element to be fixed,
    the grip element and the securing element being linked in frictional rotation via a spring of helicoidal type of which the end turns have been assembled so as to provide said spring with a substantially toroidal shape,
    two parts of the same turn, located on either side of a median plane, are inclined on the same side with respect to the radial axis of the spring.

2. Dynamometric key according to claim 1, wherein the turns of the spring, when the spring is in the free state, have a flattened shape along the radial axis thereof.

3. Dynamometric key according to claim 1, wherein the spring is compressed along its radial axis.

4. Dynamometric key according to claim 1, wherein the securing element is constituted by a cylindrical element comprising a cylindrical outer groove in which is fitted the spring, the base diameter of the groove being slightly greater than the inner diameter of the spring when the spring is in the free state.

5. Dynamometric key according to claim 4, wherein the grip element has a cylindrical recess hollowed out therein, a diameter of the cylindrical recess defines, with the diameter of the securing element, a spacing less than the height of the turns when the spring is in the free state, so as to compress the turns.

6. Dynamometric key according to claim 1, wherein the grip element comprises two parts, namely a substantially cylindrical upper part and a lower part substantially in the form of a bell.

7. Dynamometric key according to claim 6, wherein the internal volume of the bell-shaped part is such that it has the capacity to envelop the element to be fixed, whatever the positioning thereof inside the bell.

8. Dynamometric key according to claim 1, wherein the spring holds the securing element with respect to the grip element in the axial direction.

9. Dynamometric key according to claim 2, wherein the spring is compressed along its radial axis.

10. Dynamometric key according to claim 2, wherein the securing element is constituted by a cylindrical element comprising a cylindrical outer groove in which is fitted the spring, the base diameter of the groove being slightly greater than the inner diameter of the spring when the spring is in the free state.

11. Dynamometric key according to claim 3, wherein the securing element is constituted by a cylindrical element comprising a cylindrical outer groove in which is fitted the spring, the base diameter of the groove being slightly greater than the inner diameter of the spring when the spring is in the free state.

* * * * *